United States Patent [19]

Pell

[11] Patent Number: 4,919,127
[45] Date of Patent: Apr. 24, 1990

[54] ENDOTRACHEAL TUBE CONNECTOR

[76] Inventor: Donald M. Pell, 861 Sixth Ave. S., St. Petersburg, Fla. 33701

[21] Appl. No.: 189,714

[22] Filed: May 3, 1988

[51] Int. Cl.⁵ ............................................. A61M 16/00
[52] U.S. Cl. .................................. 128/207.14; 128/912
[58] Field of Search ...................... 128/200.26, 204.18, 128/207.14, DIG. 912; 604/905

[56] References Cited

U.S. PATENT DOCUMENTS

| | | | |
|---|---|---|---|
| 2,638,096 | 5/1953 | Waldhaus | 128/348 |
| 3,399,668 | 9/1968 | Lundgren | 128/2 |
| 3,880,168 | 4/1975 | Berman | 128/351 |
| 3,973,569 | 8/1976 | Sheridan | 128/351 |
| 4,146,034 | 3/1979 | Gupta | 128/351 |
| 4,369,991 | 1/1983 | Linder | 604/905 |
| 4,593,690 | 6/1986 | Sheridan et al. | 128/204.18 |
| 4,683,879 | 8/1987 | Williams | 128/200.26 |
| 4,723,543 | 2/1988 | Beran | 128/207.14 |

OTHER PUBLICATIONS

"Anaesthetic Equipment Physical Principles and Maintenance", by C. S. Ward, 1975, pp. 114–115.

Primary Examiner—Edgar S. Burr
Assistant Examiner—Aaron J. Lewis
Attorney, Agent, or Firm—Bacon & Thomas

[57] ABSTRACT

An improved connector for coupling an endotracheal tube or the like to a source of gas is disclosed. The connector has an inside diameter which is 2½ to 3 times greater than the inside diameter of the outlet and is adapted to receive a flexible tube therein. The connector also includes an intermediate portion defining a radially flared outwardly extending annular passageway and a shoulder adjacent to the larger end of the radially flared passageway. The shoulder has a width which is approximately equal to the wall thickness of the flexible tube.

8 Claims, 1 Drawing Sheet

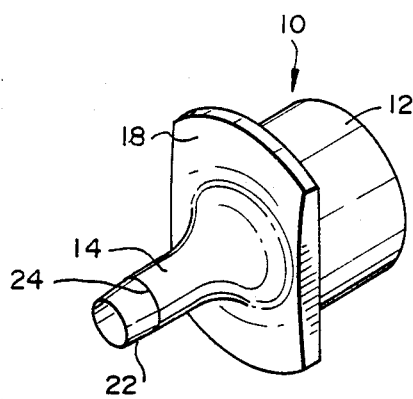
FIG_1
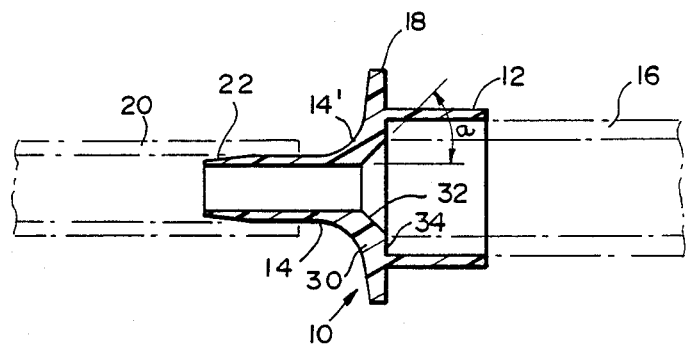
FIG_2
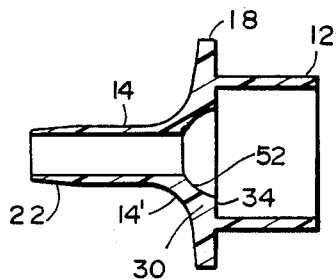
FIG_4
FIG_3
PRIOR ART
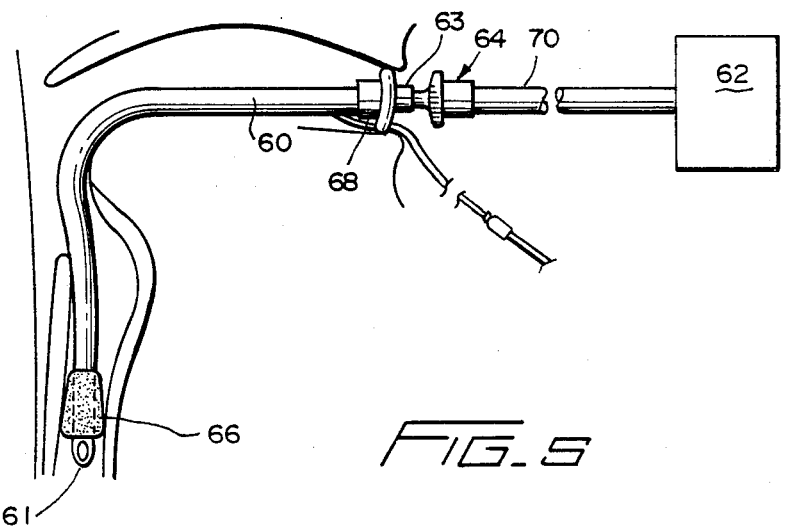
FIG_5

ENDOTRACHEAL TUBE CONNECTOR

BACKGROUND OF THE INVENTION

The present invention relates to an endotracheal tube connector for connecting an endotracheal tube to a source of oxygen or other gas, and more particularly to an endotracheal tube connector having a relatively large gas inlet and a generally funnel shaped portion for reducing the work of breathing by an intubated patient.

In general, the endotracheal tube connectors in current use have a common configuration. For example, the configuration consists basically of a pair of cylindrical barrels which share a common longitudinal axis. The first barrel, i.e. the gas inlet, has an outside diameter of about 15 mm and is adapted to receive a flexible tube having an inside diameter of about 15 mm forced over the barrel for connecting the endotracheal tube to a source of oxygen.

The second barrel, or gas outlet, of the currently used connectors has an inside diameter of about 8 mm which is the same as the inside diameter of an endotracheal tube. One end of the endotracheal tube, i.e. the end that protrudes from the mouth of a patient, is forced over the second barrel in order to insure an airtight fit, maximum gas flow and minimum resistance. In fact, the outside diameter of the outlet barrel is typically tapered at the patient end to facilitate insertion of the tubular member into the endotracheal tube and minimize turbulence as the gas passes from the connector into the endotracheal tube.

A number of problems with currently used configurations have arisen. For example, it is sometimes difficult to insert the connector into an endotracheal tube. Gupga U.S. Pat. No. 4,146,034 addresses this problem by providing a bevelled cut from the top of the connector to a point between the center line of the connector and the bottom thereof. Thus, the bevelled edge taken together with the tapered portion facilitates attaching the connector to an endotracheal tube and tends to minimize air turbulence as the gas flows from the connector into the endotracheal tube.

However, it appears that none of the prior art addresses the more serious problem which relates to the work of breathing with an endotracheal tube in place and the difficulty in removing seriously ill patients from a respirator. Removing a weakened patient from a respirator requires a patient to breath on their own and overcome the resistance of the tube and the connector. Also, it is frequently necessary to have the patient inhale oxygen enriched air and or a gas containing medication. Apparently, no one has addressed the problem of minimizing obstructions and air turbulence at the inlet end of the connector or as the oxygen enriched air is pulled or inhaled into and through the connector.

It has now been found that an improved connector according to the present invention can significantly reduce the work of breathing by reducing the negative pressure required to inhale a given volume of oxygen enriched gas. It has also been found that connectors in accordance with the present invention can be readily used with most commercially available endotracheal tubes, are relatively inexpensive to produce and relatively easy to attach to an endotracheal tube and/or to a source of oxygen or medicated vapor as selected by the physician.

In addition, the connectors disclosed herein take optimum advantage of the basic physical considerations to reduce as much as possible the resistance to breathing a patient experiences when a tracheal tube is positioned in his or her trachea and attached to a source of oxygen or the like, and thereby reduces patient discomfort, trauma and may avoid life threatening consequences.

SUMMARY OF THE INVENTION

In essence, an endotracheal tube connector according to the present invention, comprises an integral one-piece element having a pair of cylindrically shaped tubular portions which have a common longitudinal axis. For convenience the tube portions are referred to as a gas inlet and gas outlet with the gas inlet closest to a source of oxygen or other gas and the outlet extending downstream from the inlet and closest to the patient. The first portion has a relatively large inside diameter which is adapted to receive a flexible tube therein for connection to a source of oxygen. The inside diameter of the first portion is relatively large with respect to the inside diameter of the second portion, i.e. about $2\frac{1}{2}$ to 3 times greater than the inside diameter of the outlet portion.

The connectors according to the present invention also include an intermediate portion between the gas inlet and gas outlet portions. The intermediate portion defines an annular radially flared outwardly extending or generally funnel shaped passageway which shares a common longitudinal axis with the inlet and outlet and with the larger shaped end of the funnel shaped passageway adjacent the tubular inlet. The intermediate portion in a preferred embodiment of the invention also defines a shoulder or flange adjacent the larger end of the funnel shaped passageway for abuttment by a flexible tube which is connected to a source of oxygen or the like. In the preferred embodiment, the width of the shoulder is approximately the same as the wall thickness of the flexible tubing, so that, there is a relatively smooth unobstructed flow of gas with minimal turbulence through the connector.

In addition, the connector also includes a patient end portion of the outlet which shares a common longitudinal axis with the cylindrical outlet and extends downstream therefrom. The patient end portion defines a tapered outside diameter terminating at a thin circular leading edge, so that, one end of an endotracheal tube which extends outside of the patient can be forced over the tapered portion of the outlet to provide a relatively smooth obstruction-free passageway from the connector to the endotracheal tube whereby the work required for breathing is minimized.

BRIEF DESCRIPTION OF THE DRAWINGS

The invention will now be described by referring to the accompanying drawings wherein:

FIG. 1 is a perspective view which illustrates a preferred embodiment of an endotracheal tube connector according to the present invention;

FIG. 2 is a cross-section view of the connector shown in FIG. 1;

FIG. 3 is a side elevational view of a typical prior art connector;

FIG. 4 is a cross-sectional view illustrating a second embodiment of the invention; and, FIG. 5 is a side elevational view showing a combination of an endotracheal tube, source of oxygen and a connector in accordance with the present invention.

DESCRIPTION OF THE INVENTION

Referring now to the drawings, FIGS. 1 and 2 illustrate an endotracheal tube connector according to a preferred embodiment of the invention. The connector 10 is an integral one-piece element which includes a pair of cylindrically shaped tubular portions 12 and 14. The tubular portion 12 defines a gas passageway that may be referred to as the gas inlet or gas inlet portion, while portion 14 which also defines a gas passageway may be referred to as the gas outlet or gas outlet portion. The two portions 12 and 14 share a common longitudinal axis and are aligned with the outlet portion 14 downstream from inlet portion 12.

The tubular portion 12 or gas inlet has a relatively large inside diameter and is adapted to receive a flexible tube 16 having an outside diameter which is about the same as the inside diameter of portion 12. The flexible tube 16 is connected to a source of oxygen or other gas which is not shown in FIG. 1 or 2. The flexible tube 16 is forced into the tubular portion 12 and forms an air tight fit therewith.

The connector 10 also includes an outwardly extending flange 18 which is disposed between the tubular portions 12 and 14. The flange 18 has been found to be helpful in holding or positioning the connector and the flexible tube 16 is forced into the tubular portion 12. This flange 18 is also used in a similar manner when one end of an endotracheal tube 20 is forced onto the tubular portion 14.

The outside diameter of the gas outlet portion 14 is reduced in a tapered outlet end portion 22 which begins at a circumferential line 24 around the outlet portion 14. This tapered outlet end portion facilitates insertion of the connector 10 into the endotracheal tube 20, and provides for a smooth turbulent free flow of oxygen or other gas from the connector and into the endotracheal tube 20.

As shown more clearly in FIG. 2, the connector 10 includes an intermediate portion 30 which defines a radially flared axially extending annular passageway 32 which is referred to for convenience or a generally cone shaped or funnel shaped passageway. The passageway 32 shares a common longitudinal axis with the tubular portion 12 and 14 and connects the interiors thereof. The funnel shaped passageway 32 provides an elongated taper which forms an interior angle with respect to the longitudinal axis of between about 30° and 50° and preferably about 45°. This reference to the interior angle is based on extrapolating the wall of the funnel shaped passageway to the longitudinal axis of the connector or to an extension of the wall of the interior passageway of outlet 14 and is shown as angle alpha in FIG. 2.

The intermediate portion 30 also includes a shoulder 34 which lies adjacent to the base or larger end of the generally funnel shaped passageway 32. Shoulder 34 has a width which is approximately equal to the wall thickness of the flexible tube 16. Therefore, when the flexible tube 16 is forced into the tubular portion 12 with its end abutting shoulder 34 the outer edge of the funnel shaped passageway 32 is flush with the interior passage provided by flexible tube 16. This arrangement provides for a relatively unobstructed turbulent free flow of gas with a minimal effort by an intubated patient.

In applicant's device, the tubular portion 14 also includes an enlarged segment 14' which provides additional structural support between the tubular portion 14 and the tubular portion 12. The enlarged segment 14' is downstream from flange 18 and avoids structural weakness which might have been caused by the elongated funnel shaped passageway 32.

Applicant's connectors may be produced from any suitable rigid or semi-rigid material as will be understood by those skilled in the art. However, in its preferred form, the connectors are molded as a one piece element from a thermoplastic such as nylon, polyethylene or polypropylene.

The reductions in airway resistance obtained by using applicant's connector are illustrated by the following table wherein the endotracheal tubes are commonly available tubes and the standard adaptors are those which are furnished with those tubes. All pressures are in centimeters of water and LPM stands for liters per minute. In other words, the pressures indicated are the pressures required to draw the indicated liters per minute through the tubes and adaptors and through the adaptors alone for comparison. The results of replacing the standard adaptors with applicant's connector are illustrated with reference to the right hand column as illustrated therein the work of breathing at the level of 30 liters per minute has been reduced by 20 to 42.8%.

| | ALL ENDOTRACHEAL TUBES ARE 8.0 MM I.D. | | | |
|---|---|---|---|---|
| | PRESSURE* WITH TUBE AND STANDARD CONNECTOR | PRESSURE WITH STANDARD CONNECTOR | PRESSURE USING APPLICANT'S CONNECTOR | PERCENT REDUCTION OF AIRWAY RESISTANCE (PRESSURE GENERATED) |
| TUBE A | | | | |
| 30 LPM | 1.5 | .7 | 1.2 | 20% |
| 60 LPM | 5.5 | 3.7 | 5.2 | 5.4% |
| 90 LPM | 11.5 | 6.5 | 11.1 | 3.4% |
| TUBE B | | | | |
| 30 LPM | 1.4 | .6 | 1.0 | 42.8% |
| 60 LMP | 5.0 | 3.1 | 4.8 | 4% |
| 90 LPM | 10.1 | 6.5 | 10.0 | 1% |
| TUBE C | | | | |
| 30 LPM | 1.5 | .6 | 1.2 | 20% |
| 60 LPM | 5.9 | 2.9 | 5.8 | 1.6% |
| 90 LPM | 12.3 | 6.8 | 12.0 | 2.4% |
| TUBE D | | | | |
| 30 LPM | 1.5 | .5 | 1.1 | 26.6% |
| 60 LPM | 6.0 | 2.8 | 5.2 | 13.3% |
| 90 LPM | 12.5 | 6.5 | 11.3 | 9.6% |

*ALL PRESSURES IN CENTIMETERS OF WATER.

Prior to the development of applicant's improved connector, is was believed by applicant and others that the work of breathing was dependent on the cross-sectional area of the endotracheal tube or the connector and by the length of the tube. However, it has now been found that the present device substantially reduces airway resistance, that is the reduction in work required for a patient to inhale a given volume of air in a given amount of time. By contrast a currently used connector 40 as illustrated in FIG. 3, includes a flow obstructing end portion 41 of a first tubular portion 42. This end 41 obstructs the flow of gas and creates air turbulence. In addition, a relatively abrupt transition portion 43 from tubular portion 42 to a tubular portion 44 provides a further obstruction. And, even though this obstruction may include a slight taper of about 15° to 20° with respect to the longitudinal axis, it apparently causes a significant amount of resistance.

The second embodiment of the invention which is illustrated in FIG. 4 is generally similar to the preferred embodiment. However, in the second embodiment a generally funnel shaped passageway 52 defines a concave arcuit surface of revolution.

FIG. 5 illustrates a combination of an endotracheal tube 60, source of oxygen or other gas 62 and adaptor or connector 64. In this combination the endotracheal tube 60 includes a distal end 61 adapted for intubation in a patient and a proximal end 63 which is adapted to protrude from an intubated patient mouth or nose. The endotracheal tube 60 also includes an inflatable cuff 66 at the distal end 61 and a bite block 68 which is near the proximal end of the tube.

The connector 64 shown in FIG. 5 has the same configuration as shown in FIG. 2 and is connected to the source of oxygen 6 by a flexible tube 70.

While the preferred embodiments of the invention have been illustrated and described it is to be understood that alterations and modifications may be made to the described embodiments without departing from the scope of the present inventions.

What is claimed is:

1. A connector for connecting an endotracheal tube to a source of gas, comprising an annular gas inlet and an annular gas outlet sharing a common longitudinal axis with said inlet and extending downstream therefrom; said inlet having an inside diameter which is about 2½ to 3 times greater than the inside diameter of said outlet and adapted to receive a flexible tube having an outside diameter which is approximately the same as the inside diameter of said inlet therein, and an intermediate portion between said inlet and said outlet defining a radially flared outwardly extending annular passageway sharing a common longitudinal axis with said inlet and said outlet and connecting said inlet and said outlet with the smaller end of said radially flared passageway adjacent to the inside of said outlet, means to minimize turbulence and thereby reduce the work of breathing including a shoulder adjacent to the larger end of said radially flared passageway, said shoulder having a width approximately equal to the wall thickness of the flexible tube, so that, when the flexible tube is inserted into the inside of said inlet with its end abutting said shoulder, the outer edge of the large end of said radially flared passageway is flush with the interior passage provided by the flexible tube to thereby provide a smooth relatively unobstructed flow of gas through the tube and the connector, and a patient end portion of said outlet sharing a common longitudinal axis with said cylindrical outlet means and extending downstream therefrom, said patient end portions having a tapered outside diameter terminating at a thin circular leading edge so that one end of an endotracheal tube which extends outside of the patient can be forced over the tapered portion of the outlet to provide a relatively smooth obstruction free passageway from and through the connector to the endotracheal tube whereby the work of inspiration by an intubated patient is minimized.

2. A connector for connecting an endotracheal tube or the like to a source of gas according to claim 1 wherein the ratio of the inside diameter of said gas inlet to the inside diameter of said gas outlet is about 2.75:1.

3. A connector for connecting an endotracheal tube or the like to a source of gas according to claim 1 in which said intermediate portion defines a passageway having a frustoconical shape, and in which the wall of the frustoconical passageway forms an interior angle with respect to the longitudinal axis of the passageway of between about 30° to about 50°.

4. A connector for connecting an endotracheal tube or the like to a source of gas according to claim which includes flange means extending from the periphery of said inlet.

5. A connector for connecting an endotracheal tube or the like to a source of gas according to claim 2 in which said intermediate portion defines a passageway having the shape of a concave arcuate surface of revolution.

6. A connector for connecting an endotracheal tube or the like to a source of gas according to claim 4 wherein the connector is an integral one piece thermoplastic element wherein the inside diameter of said gas inlet is about 22 mm, the inside diameter of said outlet is about 8 mm and the length of said inlet, intermediate and outlet portions are about, 17 mm, 8 mm and 25 mm respectively and wherein the length of the tapered portion is about 8 mm.

7. The combintion of an endotracheal tube having a distal end adapted for intubation in a patient and a proximal end adapted to protrude from an intubated patient's mouth or nose, a source of oxygen and a connector for connecting the proximal end of the endotracheal tube to the source of oxygen; said connector comprising an integral one piece element having a first cylindrical tubular portion and a second cylindrical tubular portion sharing a common longitudinal axis with said first cylindrical tubular portion and extending downstream therefrom, said first cylindrical tubular portion having an inside diameter which is about 2½ to 3 times the inside diameter of said second cylindrical tubular portion and said first cylindrical tubular portion including an external flange extending outwardly from the periphery thereof, and an intermediate portion between said first cylindrical tubular portion and said second cylindrical tubular portion defining an elongated radially flared outwardly extending annular passageway sharing a common longitudinal axis with said first and second cylindrical tubular portions and connecting said first and second cylindrical tubular portions with the smaller end of said radially flared outwardly extending annular passageway adjacent to the inside of said second cylindrical tubular portion, means to minimize turbulence and thereby reduce the work of breathing including an internal shoulder adjacent to the first cylindrical tubular portion and to the base or larger portion of the radially flared outwardly extending passageway and extending around the inside of the first cylindrical tubular portion, a flexible tube having an outside diameter which is approximately the same as the inside diameter of said first cylindrical tubular portion extending between said source of oxygen and said connector with a first end connected to said source of oxygen and with the second end forced into said first cylindrical portion with its end abutting said internal shoulder and having a wall thickness about the same as the width of said shoulder so that oxygen can flow into and through the passageway with minimum turbulence, a patient end portion of said outlet sharing a common longitudinal axis with said second cylindrical tubular portion and extending downstream therefrom, said patient end portion having a tapered outside diameter terminting at a thin circular leading edge so that the proximal end of said endotracheal tube can be forced over the tapered portion whereby the work of inspiration of an intubated patient is reduced because of the minimal turbulent and obstruction to the flow of oxygen through the connector.

8. A connector for connecting an endotracheal tube or the like to a source of gas according to claim 3 in which the internal angle formed by the wall of the passageway with respect to the longitudinal axis of the passageway is about 45°.

* * * * *